(12) United States Patent
Tawara et al.

(10) Patent No.: US 6,719,217 B1
(45) Date of Patent: Apr. 13, 2004

(54) AROMATIZER

(75) Inventors: Hirotoshi Tawara, Tokyo (JP); Takashi Yamada, Tokyo (JP); Fumihiko Yoshiro, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/868,614
(22) PCT Filed: Dec. 24, 1999
(86) PCT No.: PCT/JP99/07295
§ 371 (c)(1),
(2), (4) Date: Jun. 22, 2001
(87) PCT Pub. No.: WO00/40276
PCT Pub. Date: Jul. 13, 2000

(30) Foreign Application Priority Data

| Dec. 28, 1998 | (JP) | 10-372909 |
| Dec. 28, 1998 | (JP) | 10-372917 |
| Dec. 28, 1998 | (JP) | 10-372962 |
| Dec. 28, 1998 | (JP) | 10-372967 |
| Jan. 7, 1999 | (JP) | 11-002235 |

(51) Int. Cl.$^7$ ............................................. F23D 11/16
(52) U.S. Cl. ............... 239/419.5; 239/302; 239/379; 239/419; 261/DIG. 17; 261/DIG. 88; 422/124
(58) Field of Search .................. 239/302, 326, 239/379, 289, 419, 419.5; 261/97, 98, 115, 119.1, DIG. 17, DIG. 88; 422/123, 124

(56) References Cited

U.S. PATENT DOCUMENTS

| 2,952,606 | A | * | 9/1960 | Pascale et al. | ............ 422/186.1 |
| 3,990,848 | A | * | 11/1976 | Corris | ........................ 422/124 |
| 5,460,787 | A | * | 10/1995 | Colon | ................. 261/DIG. 88 |
| 5,562,407 | A | * | 10/1996 | Cielo | ....................... 415/121.2 |

FOREIGN PATENT DOCUMENTS

| JP | 54471 | 11/1920 |
| JP | 59-141899 | 9/1984 |
| JP | 63-135645 | 9/1988 |
| JP | 2-20550 | 2/1990 |
| JP | 2-116452 | 9/1990 |
| JP | 10-85313 | 4/1998 |
| JP | 10-314290 | 12/1998 |

\* cited by examiner

Primary Examiner—Steven J. Ganey
(74) Attorney, Agent, or Firm—Oblon, Spivak, McClelland, Maier & Neustadt, P.C.

(57) ABSTRACT

The invention provides an air fragrance device (10) having a fan (26) driven by a motor (24) and provided in a blowing chamber (35) and an air fragrance tank (13) having a fragrant agent (1) therein and communicated with the blowing chamber (35), in which the blowing chamber (35) is arranged below the air fragrance tank (13).

10 Claims, 9 Drawing Sheets

F I G. 5
(A)
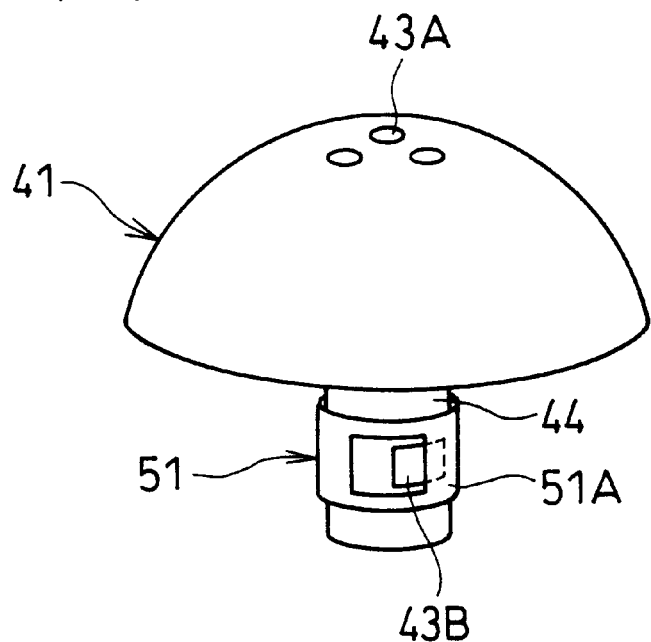
(B)
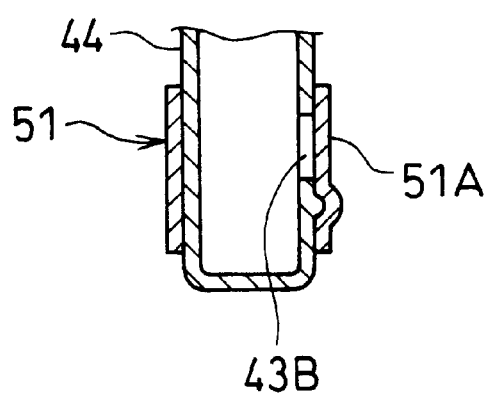
(C)
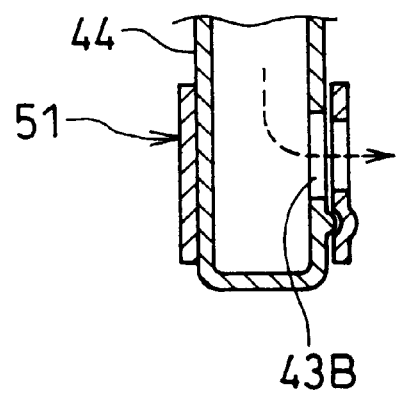

F I G. 8
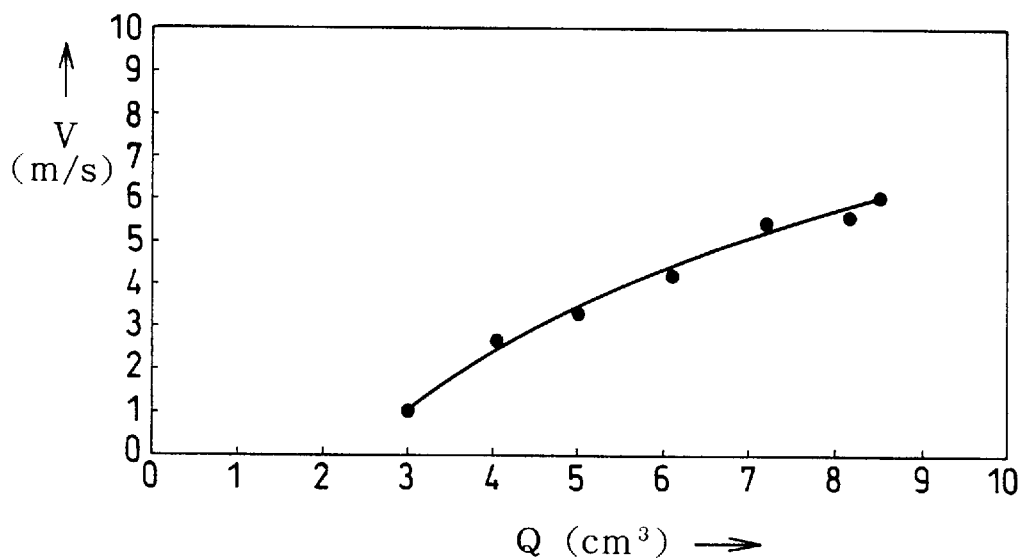

AROMATIZER

TECHNICAL FILED

The present invention relates to an air fragrance device.

BACKGROUND ART

There is an air fragrance device in which a fan driven by a motor is provided in a blowing chamber and the blowing chamber is communicated with a side portion of an air fragrance tank having a fragrant agent therein, disclosed in Japanese Patent Application Lad-Open (JP-A) No. 10-85313, the air fragrance device being placed within a room or the like.

The air fragrance device is structured such that when the fan is driven, a residence air in the blowing chamber is at first discharged and thereafter a fragrant smell (an air containing a fragrant material) in the air fragrance tank side is discharged via the blowing chamber. Accordingly, it is impossible to immediately discharge the fragrant smell together with the driving operation of the fan.

DISCLOSURE OF THE INVENTION

An object of the present invention is to discharge a fragrant smell immediately after starting driving a fan in an air fragrance device.

In accordance with the present invention, there is provided an air fragrance device comprising: a fan driven by a motor and provided in a blowing chamber; and an air fragrance tank having a fragrant agent therein and communicated with the blowing chamber, wherein the blowing chamber is arranged below the air fragrance tank.

BRIEF DESCRIPTION OF THE DRAWINGS

FIG. 5 is a schematic view showing a receiving cassette for a fragrant material;

FIG. 8 is a graph showing an air fragrance blowing characteristic;

BEST MODE FOR CARRYING OUT THE INVENTION (Fist Embodiment) (FIGS. 1 to 5)

Figure 1:
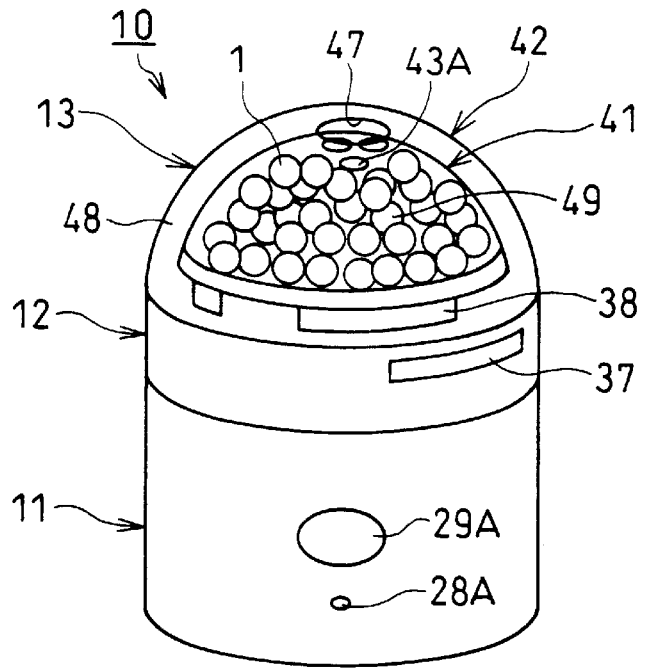
FIG. 1 is a perspective view showing an air fragrance device.
Figure 2:
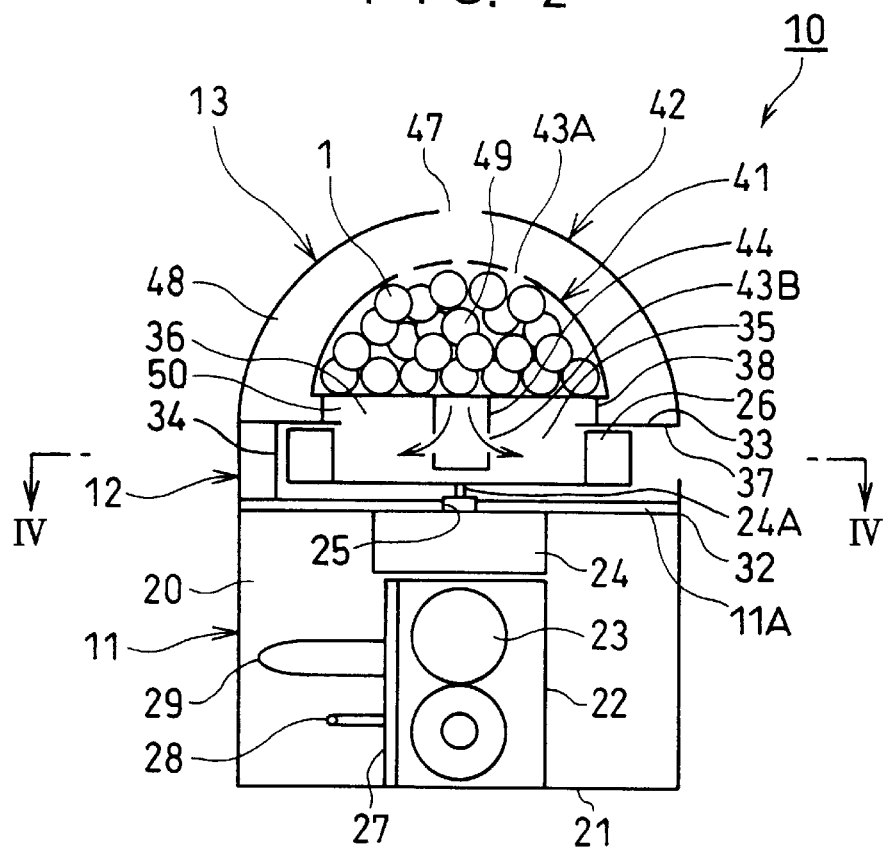
FIG. 2 is a cross sectional view showing an air fragrance device.

An air fragrance device 10 corresponds to a three-layer structure body obtained by layering a motor case 11, a blowing case 12 and an air fragrance tank 13, as shown in FIGS. 1 and 2.

The motor case 11 is structured such that a bottom cover 21 is fitted to a bottom portion of a drive circuit chamber 20 constituted by a cylindrical body with a top, and a battery 23 is received in a battery receiving portion 22 integrally formed with the bottom cover 21. The bottom cover 21 is structured such that an engaging portion provided on an outer periphery is engaged with and attached to an inner periphery of the bottom portion of the motor case 11. A motor 24 is mounted on an upper surface of the bottom cover 21, an output shaft 24A of the motor 24 passes through an axial hole 25 provided on a top surface of a shielding plate 11A in the motor case 11, and a fan 26 is pressure inserted to a through end. A drive circuit board 27 for the motor 24 is attached to a side surface of the battery receiving portion 22 provided in the bottom cover 21, an operation lamp 28 of the motor 24 and a sensor 29 detecting a human body so as to drive the motor 24 is provided in the drive circuit board 27, and a lamp window 28A and a sensor window 29A respectively corresponding to the lamp 28 and the sensor 29 are provided on a side surface of the motor case 11.

The blowing case 12 is structured such that an inner periphery of a lower end of a short cylindrical body is engaged with an annular groove 32 provided in the outer periphery of the top end of the motor case 11. The blowing case 12 is provided with an upper partition plate 33 provided in an inner periphery of an upper end and a substantially C-shaped side partition plate 34 provided in a lower surface of the upper partition plate 33. Accordingly, the blowing case 12 forms a blowing chamber 35 surrounded by the top surface of the motor case 11, the upper partition plate 33 and the side partition plate 34 in a state of being engaged with the motor case 11, arranges the fan 26 mentioned above in a center of the blowing chamber 35, arranges a suction port 36 provided in a center of the upper partition plate 33 above the center of the fan 26, and arranges a blowing port 37 provided in a side surface of the blowing case 12 corresponding to a portion between both substantially C-shaped end portions of the side partition plate 34 in an outer peripheral side of the blowing chamber 35.

The air fragrance tank 13 is constituted by a fragrant material receiving cassette 41 and a cover 42. The fragrant material receiving cassette 41 is formed in a semispherical shape with a bottom, and constituting a fragrant material receiving portion for receiving a fragrant material 1 (a fragrant agent). The fragrant material receiving cassette 41 is structured such that one or more inlets 43 are opened on a spherical top surface, a cylinder portion 44 with a bottom is communicated with a center of the bottom surface, and an outlet 43B is opened to a cylinder side surface of the cylinder portion 44. The fragrant material receiving cassette 41 is mounted on a support protruding portion 38 disposed on the upper surface of the upper partition plate 33 of the blowing case 12, and the cylinder portion 44 is arranged in the suction port 36 in a center of the upper partition plate 33. In this case, the fragrant material receiving cassette 41 prevents particulate objects of the fragrant material 1 from flowing out into the cylinder portion 44 with a bottom by means of a net (not shown) placed in an inner side of the bottom surface. The cover 42 is formed in a semispherical cup shape, is engaged with and disengaged from the blowing case 12 by an engaging portion 45 provided in an outer periphery of the lower end. The cover 42 is provided with an air intake port 47 on a spherical top surface, and forms an air intake passage 48 between the outer surface of the fragrant material receiving cassette 41 and the cover 42 in a state of being engaged with and attached to the blowing case 12 (the air intake passage 48 extends to the suction port 36 between the bottom surface of the fragrant material receiving cassette 41 and the upper surface of the upper partition plate 33 in the blowing case 12).

The air fragrance device 10 is structured such that when the human body is detected by the sensor, the motor 24 is turned on so as to drive the fan 26. In accordance with the driving operation of the fan 26, the air is sucked into the blowing chamber 35 from the suction port 36 via the air intake passage 48 passing through the portion between the cover 42 and the fragrant material receiving cassette 41 from the air intake port 47 of the cover 42, and the fragrant smell within the fragrant material receiving cassette 41 is sucked into the blowing chamber 35 from the suction port 36 by a fragrant smell intake passage 49 passing through an inlet 43A and an outlet 43B of the fragrant material receiving cassette 41 from the air intake port 47 in the cover 42. Accordingly, the air and the fragrant smell are mixed in the blowing chamber 35 so as to generate a fragrant smell and blown out from the blowing port 37 in the side surface of the blowing case 12.

The air fragrance device 10 is structured such that the fan 26 driven by the motor 24 is provided in the blowing chamber 35, and the blowing chamber 35 having the blowing port 37 below the air fragrance tank 13 at a time of communicating the air fragrance tank 13 receiving the fragrant material 1 with the blowing chamber 35 via the fragrant smell intake passage 49 as mentioned above.

That is, in the air fragrance device 10, in order to utilize a nature that the fragrant smell drops down due to an effect of gravity, the air fragrance tank 13 is provided above the blowing chamber 35. Accordingly, the fragrant smell generated from the air fragrance tank 13 moves downward to the below blowing chamber 35 so as to stay, so that when driving the fan 26 by the motor 24, it is possible to immediately blow out the fragrant smell from the blowing port 37. This is particularly preferable in the present embodiment structured such that the human body is detected by the sensor and the fragrant smell is output.

Figure 3:
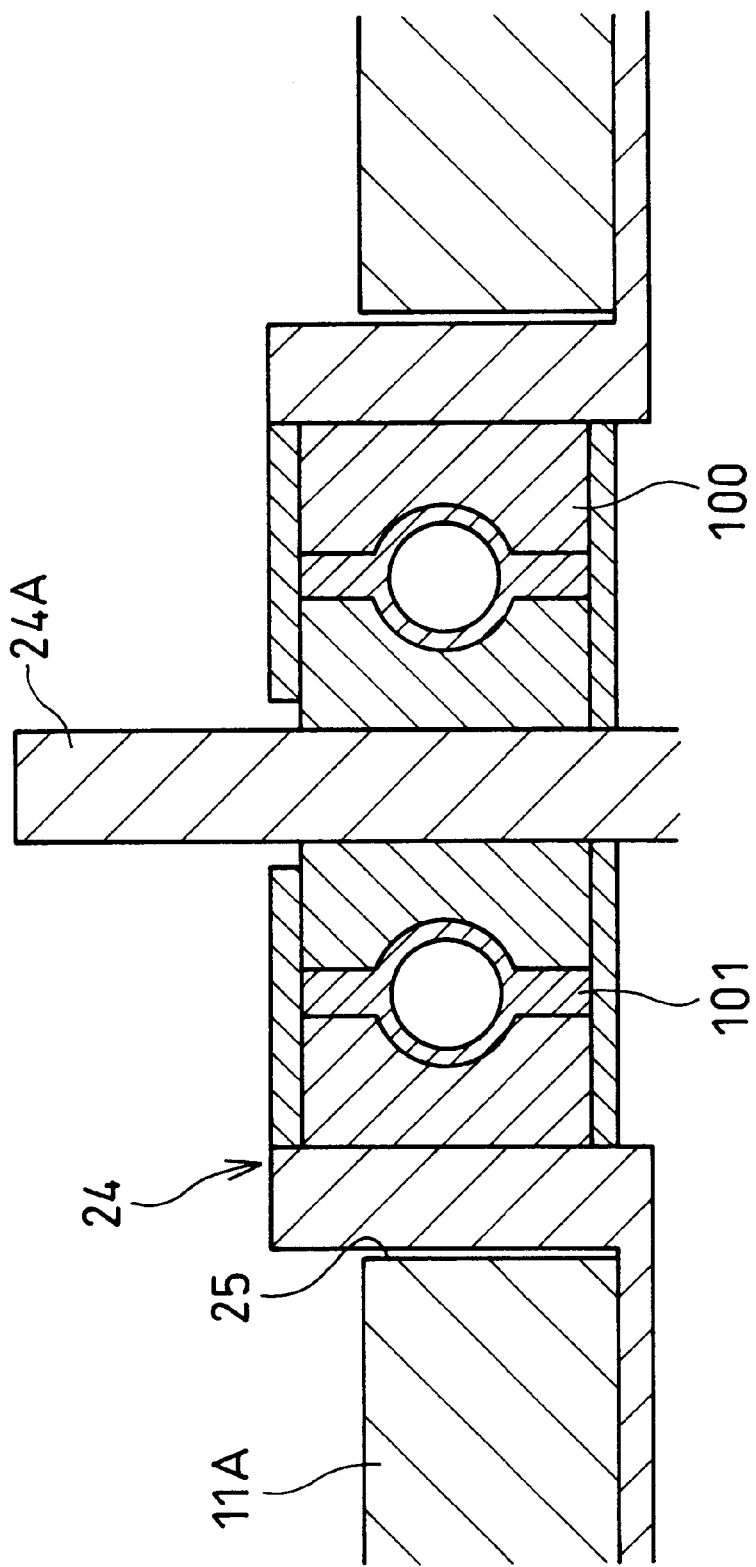
FIG. 3 is a schematic cross sectional view showing a support structure for a motor shaft.

Further, in the air fragrance device 10, as shown in FIG. 3, a bearing 100 pivotally supporting the output shaft 24A is provided in a frame top surface of the motor 24, and the bearing 100 supports the output shaft 24A of the motor 24, thereby preventing the output shaft 24A from oscillating at a time of rotating, and a grease 101 charged into the bearing 100 prevents the fragrant smell from leaking into the motor 24.

Further, the air fragrance device 10 is structured such that the air intake passage 48 passing through the portion between the cover 42 and the fragrant material receiving cassette 41 from the air intake port 47 of the cover 42, and the fragrant smell intake passage 49 passing through the inlet 43A and the outlet 43B of the fragrant material receiving cassette 41 from the air intake port 47 of the cover 42 are communicated with the suction port 36 of the blowing chamber 35 in which the fan 26 driven by the motor 24 is arranged, and the blowing port 37 of the blowing chamber 35 is provided on the side surface of the blowing case 12, whereby a blowing path 50 is constituted by the air intake passage 48, the fragrant smell intake passage 49, the suction port 36 of the blowing chamber 35 and the blowing port 37 thereof. On the other hand, the drive circuit chamber 20 installing the motor 24 and the drive circuit board 27, and the battery receiving portion 22 receiving the battery 23 are provided in the inner portion of the motor case 11, and the drive circuit chamber 20 and the battery receiving portion 22 are shielded with respect to the blowing path 50 by the shield plate 11A formed by the top surface of the motor case 11 and the bearing 100 around the axial hole 25.

That is, in the air fragrance device 10, the drive circuit chamber 20 in which the motor 24 is arranged, is shielded from the blowing path 50 in which the fragrant material 1 stays. Accordingly, it is possible to protect a brush or the like of the motor 24 from an abnormal abrasion, a corrosion or the like due to the fragrant material 1 being attached thereto, and it is possible to secure a stability of a air fragrance operation due to a smooth operation of the fan 26.

Further, the air fragrance device 10 is structured such that the air intake passage 48 communicated with the suction port 36 of the blowing chamber 35 in which the fan 26 is provided and the fragrant smell intake passage 49 are separately provided, and the air and the fragrant smell supplied by both the intake passages 48 and 49 are mixed by the fan 26 so as to be blown out from the blowing port 37 of the blowing chamber 35.

Figure 4:
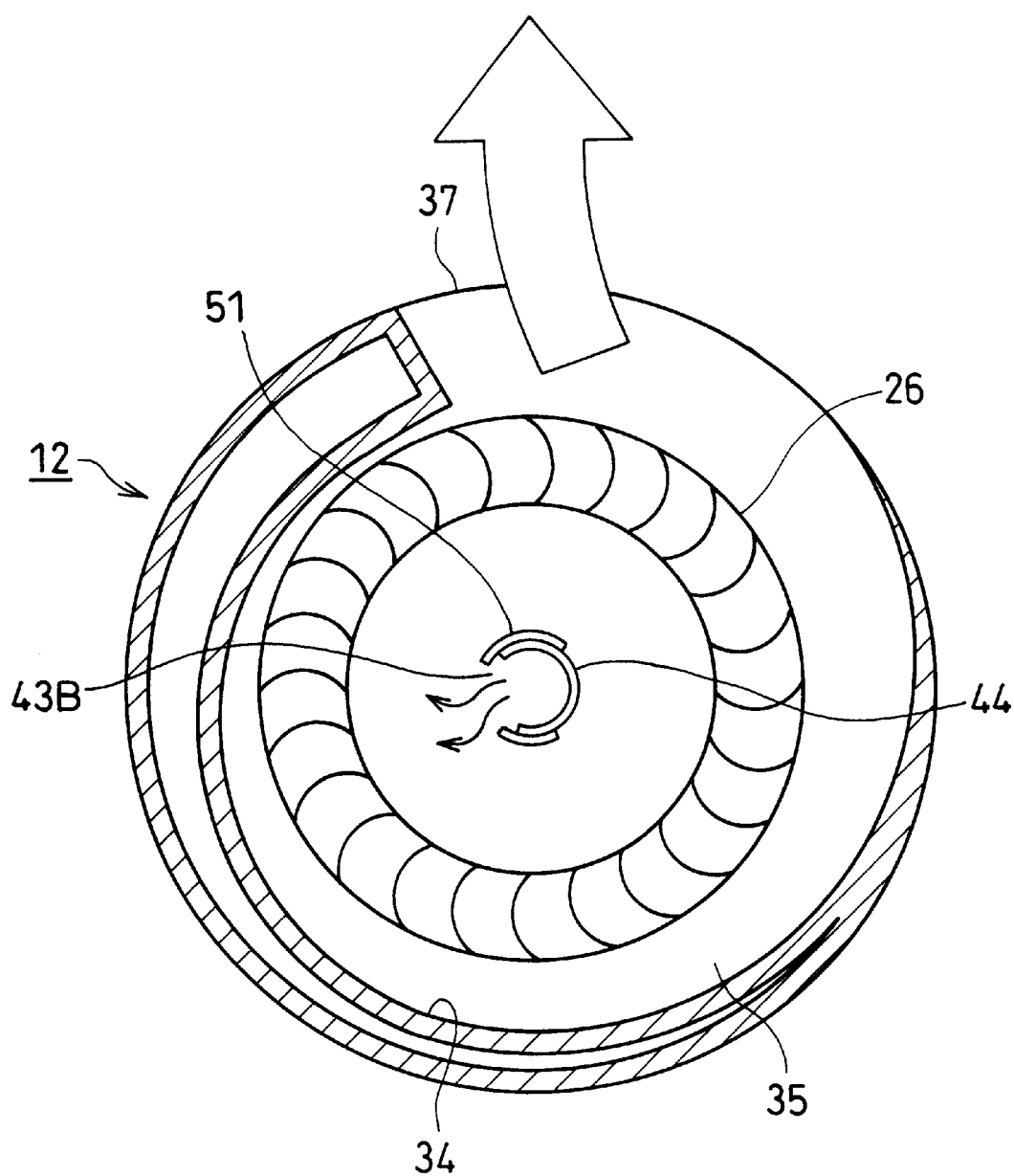
FIG. 4 is a cross sectional view along a line IV—IV in FIG. 2.

At this time, a fragrant smell flow amount adjusting valve 51 can be provided in the outlet 43B provided in the cylinder portion 44 of the fragrant material receiving cassette 41 forming the fragrant smell intake passage 49, as shown in FIGS. 4 and 5. The valve 51 is inserted and attached so as to freely rotate around the cylinder portion 44, thereby capable of adjusting an opening amount of the outlet 43B by a plate-like valve body 51A.

That is, in the air fragrance device 10, most of the air entering from the air intake port 47 of the air fragrance device 10 enters through the air intake passage 48 to the blowing chamber 35 in which the fan 26 is placed, and the other little air enters through the fragrant smell intake passage 49 to the blowing chamber 35. As mentioned above, since the air and fragrant smell intake passages 48 and 49 are separately provided, it is possible, for example, to throttle the fragrant smell intake amount while increasing the air intake amount passing through the air intake passage 48, whereby it is possible to obtain an increased amount of air fragrance blow without making the fragrant smell rich. That is, it is possible to easily adjust a density of the fragrant smell blowing out from the air fragrance device 10 by adjusting a flow passage area, a flow passage resistance or the like of both the passages 48, 49 at a stage of designing the air fragrance device 10.

Further, in the air fragrance device 10, it is possible to easily change the density of the fragrant smell without changing the air fragrance blowing out amount by providing the fragrant smell flow amount adjusting valve 51 in the fragrant smell intake passage 49, whereby it is possible to easily adjust the density of the fragrant smell blowing out from the air fragrance device 10 at a time of using the air fragrance device 10.

Figure 6:
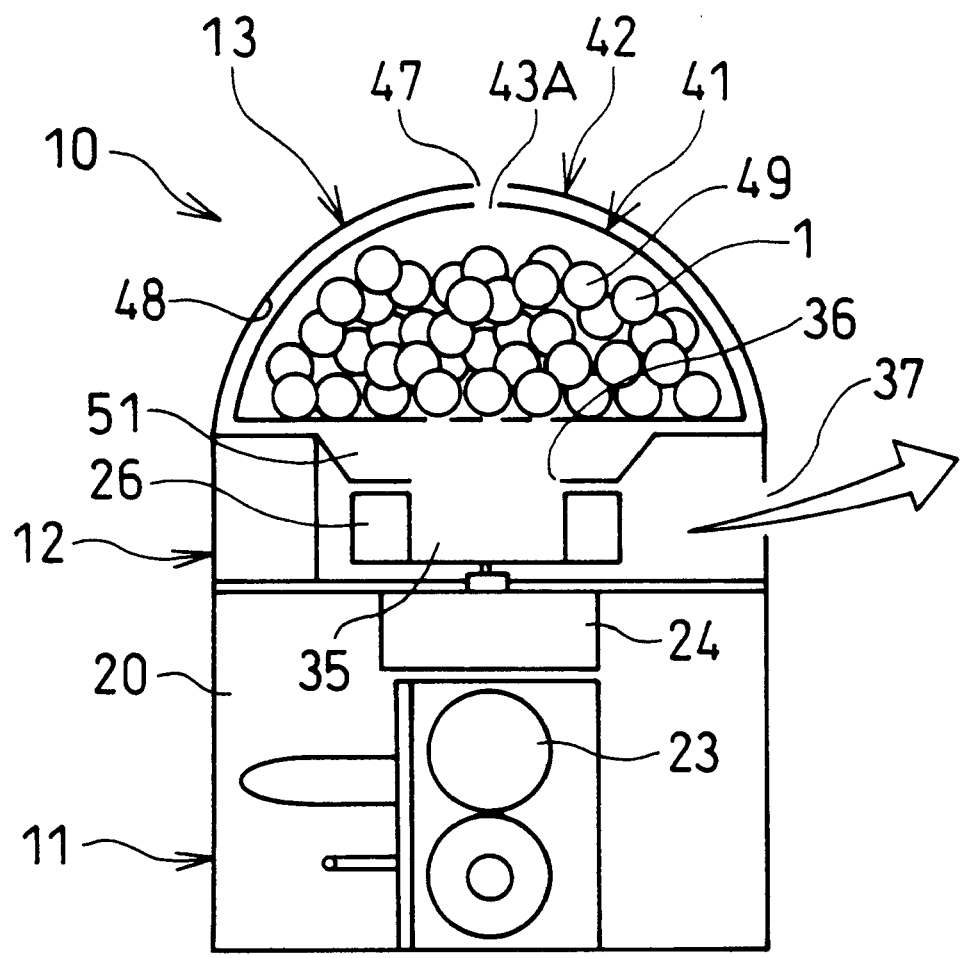
FIG. 6 is a cross sectional view showing an air fragrance device.
Figure 7:
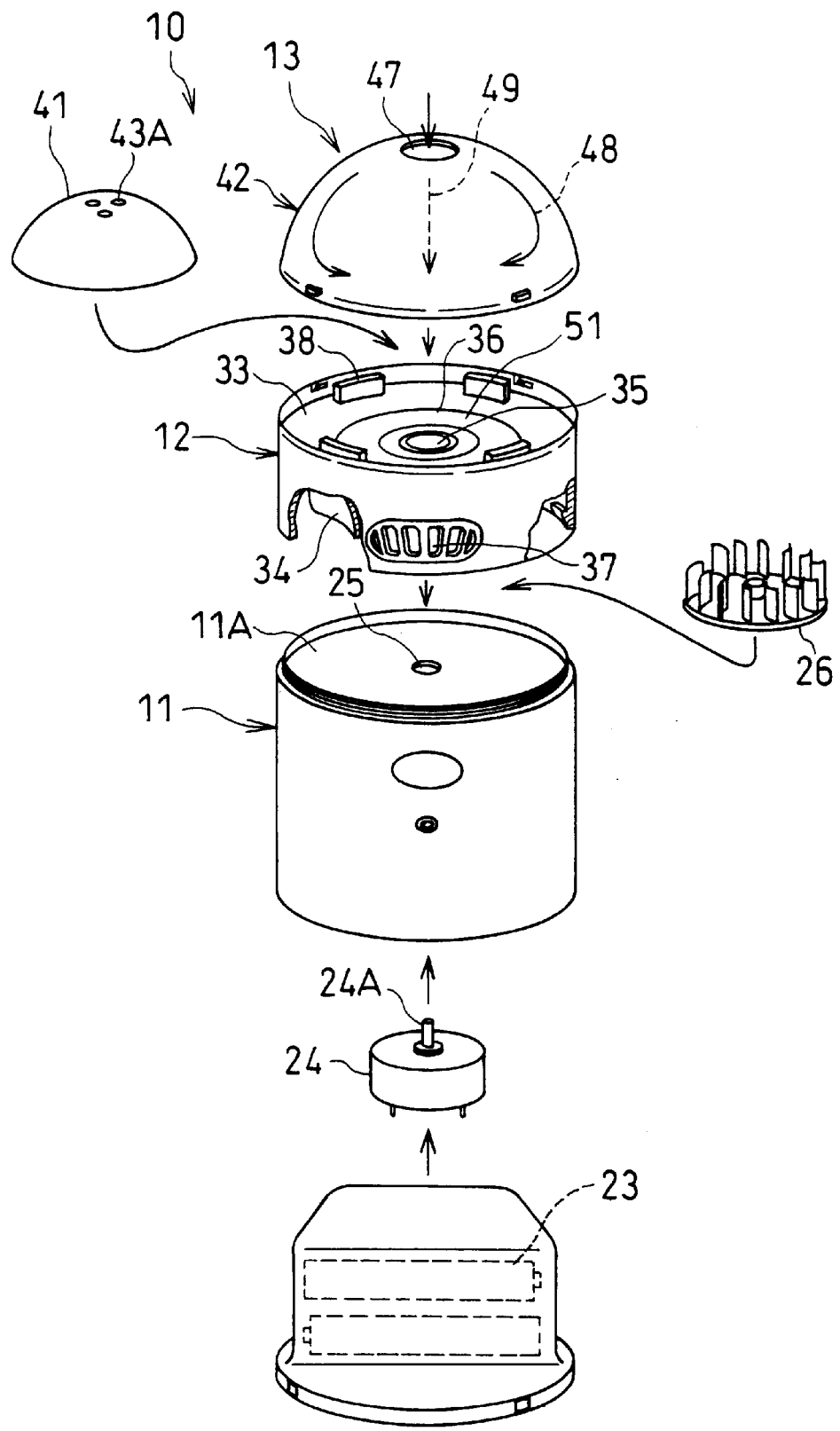
FIG. 7 is an exploded perspective view showing an air fragrance device.

(Second Embodiment) (FIGS. 6 to 8)

In the air fragrance device 10 in accordance with a second embodiment, as shown in FIGS. 6 and 7, in the blowing case 12, a recess-shaped air storage portion 51 is provided in an immediately upstream side of the suction port 36 of the blowing chamber 35 in which the fan 26 driven by the motor 24 is provided, and a narrow air intake passage 48 provided between the fragrant material receiving cassette 41 and the cover 42 (in the present embodiment, since an outer shape of the fragrant material receiving cassette 41 is as close as possible to the inner periphery of the cover 42 so as to increase a fragrant material receiving volume of the fragrant material receiving cassette 41 as much as possible, the air intake passage 48 is made narrow) is communicated with the air storage portion 51.

That is, in the air fragrance device 10, when the volume of the fragrant material receiving cassette 41 is increased, it is unavoidable that the flow passage area of the air intake passage 48 to the blowing chamber 35 formed around the fragrant material receiving cassette 41 becomes narrow, however, when the fan 26 is operated, the air is smoothly sucked from the air storage portion 51 disposed in the immediately upstream side, so that it is possible to take in a sufficient amount of air and it is possible to increase the air fragrance blowing out amount.

FIG. 8 shows experimental results using the air fragrance device 10, and shows a relation between an air fragrance blowing out speed V (m/s) blown out from the blowing port 37 of the blowing chamber 35 at a time of rotating the fan 26 and a volume Q (cm$^3$) of the air storage portion 51 mentioned above. The more the volume of the air storage portion 51 is, the more the fragrant smell blowing out speed is.

Figure 9:
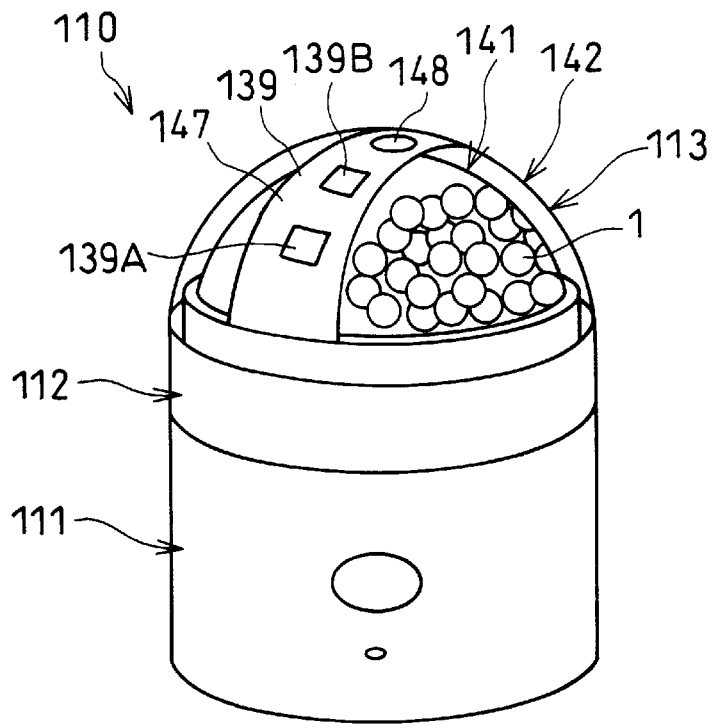
FIG. 9 is a perspective view showing an air fragrance device.
Figure 10:
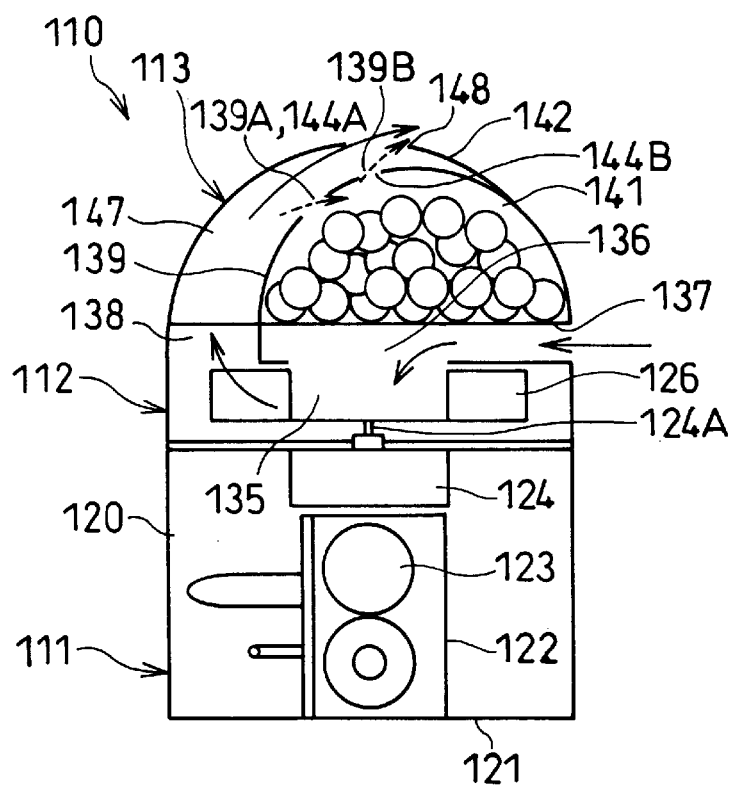
FIG. 10 is a cross sectional view showing an air fragrance device.
Figure 11:
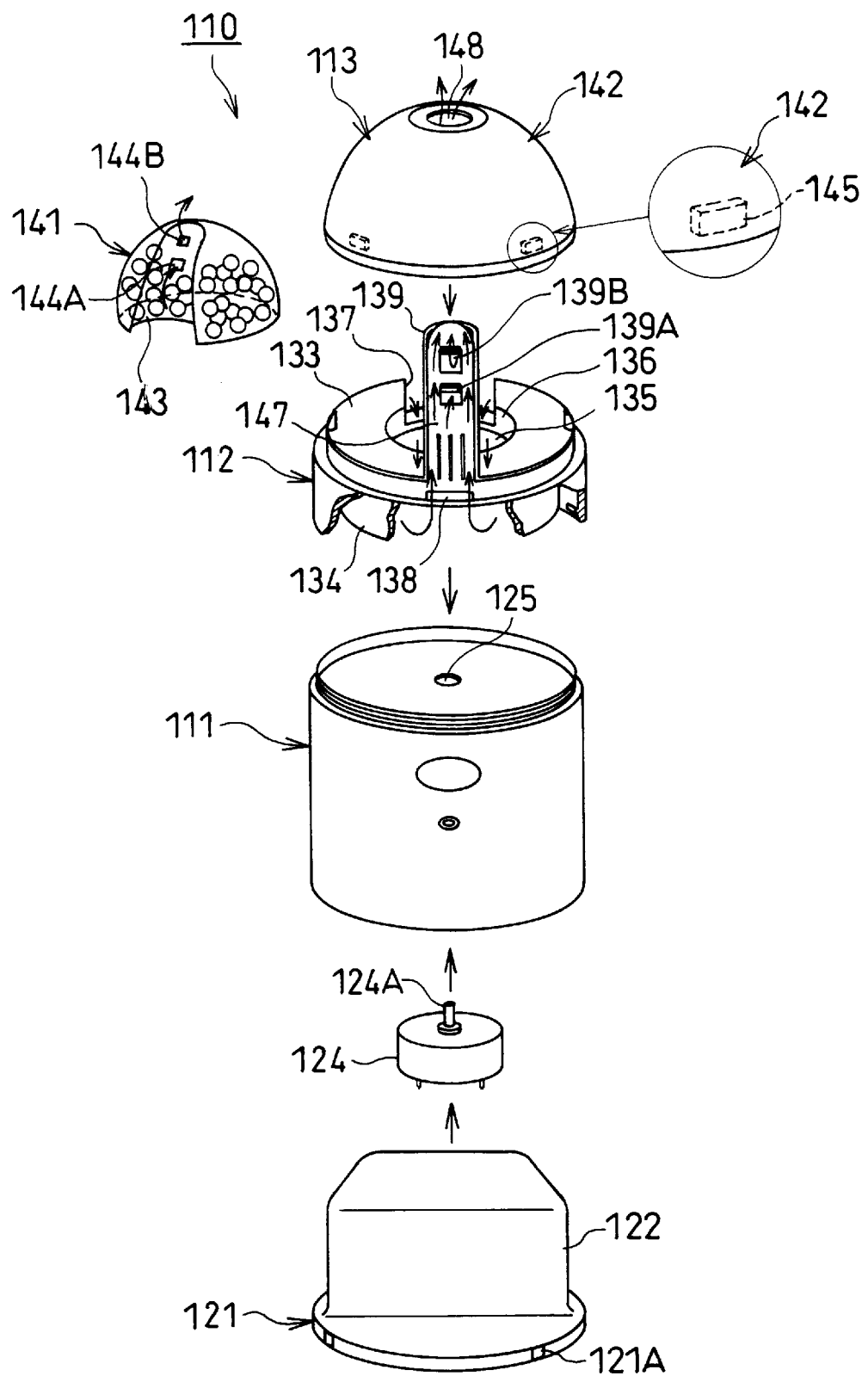
FIG. 11 is an exploded perspective view showing an air fragrance device.

(Third Embodiment) (FIGS. 9 to 11)

In a third embodiment, an air fragrance device 110 corresponds to a three-layer structure body obtained by layering a motor case 111, a blowing case 112 and an air fragrance tank 113, as shown in FIGS. 9 to 11.

The motor case 111 receives a battery 123 and a motor 124, an output shaft 124A of the motor 124 extends through an axial hole 125 provided on a top surface of the motor case 111, and a fan 126 is pressure inserted to a through end thereof.

The blowing case 112 is provided with an upper partition plate 133 provided in an inner periphery of an upper end, and a side partition plate 134 provided on a lower surface of the upper partition plate 133. The blowing case 112 is engaged with the motor case 111 and forms a blowing chamber 135 surrounded by the top surface of the motor case 111, the upper partition plate 133 and the side partition plate 134, the fan 126 mentioned above is arranged in a center of the blowing chamber 135, a suction port 136 provided in a center of the upper partition plate 133 is formed above the center of the fan 126, and an air intake port 137 provided so as to pass through the side partition plate 134 from the side surface of the blowing case 112 is communicated with the suction port 136 mentioned above. Further, the blowing case 112 has an air discharge port 138 open to the upper partition plate 133 corresponding to an outer peripheral side of the blowing chamber 135, and is provided with a blowing guide 139 extending so as to form a curved shape from a portion positioned close to the air discharge port 138 on the upper surface of the upper partition plate 133. The blowing guide 139 has a U-shaped horizontal cross section and is formed in a curved shape extending in such a manner as to be closely attached to an inner surface of a cover 142 of an air fragrance tank 113 mentioned below in both side edge portion of the U-shaped portion. The blowing guide 139 is provided with an air distribution port 139A and a fragrant smell outlet 139B.

The air fragrance tank 113 is constituted by a fragrant material receiving cassette 141 and the cover 142. The fragrant material receiving cassette 141 is formed in a substantially semispherical shape with a bottom constituted by a transparent body, and receives the fragrant material 1 (the fragrant agent). The fragrant material receiving cassette 141 is provided with a recessed portion 143 extending to the top side from the bottom side of the spherical body side surface, and fits the recessed portion 143 to a back surface of the blowing guide 139 provided in the blowing case 112 so as to be aligned therewith, thereby mounting at a predetermined position on the upper partition plate 133 of the blowing case 112. The fragrant material receiving cassette 141 is structured such that an inlet 144A is opened to the side surface of the spherical body, the outlet 144B is opened to the upper portion in the top surface side from the inlet 144A, the inlet 144A is aligned with the air distribution port 139A of the blowing guide 139 in the blowing case 112 in a state of mounting the blowing case 112 on the upper partition plate 133, and the outlet 144B is aligned with the fragrant smell outlet 139B.

The cover 142 is formed in a semispherical cup shape constituted by a transparent body, and is engaged with and disengaged from the blowing case 112 by engaging an engaging portion 145 provided in an inner periphery of the lower end with an annular protruding portion 146 provided in an outer periphery of the upper end of the blowing case 112. The cover 142 is closely attached to both side edge portions of the U-shaped portion in the blowing guide 139 provided in the blowing case 112 in a state of being closely engaged with the blowing case 112 so as to form a blowing passage 147 (a blowing path) between the blowing guide 139 and the cover 142, and a fragrant smell blowing port 148 connected to the blowing passage 147 is open to the spherical top portion. At this time, an outlet 144B of the fragrant material receiving cassette 141 is communicated with the blowing passage 147 in an immediately upstream side of the fragrant smell blowing port 148 via the fragrant smell outlet 139B of the blowing guide 139.

Accordingly, the air fragrance device 110 is structured such that the motor 124 drives the fan 126. Due to the driving operation of the fan 126, the air sucked into the blowing chamber 135 via the suction port 136 from the air intake port 137 on the side surface of the blowing case 112 is pressure fed to the blowing passage 147 of the blowing guide 139 from the air discharge port 138 of the blowing chamber 135. The air pressure fed to the blowing passage 147 partly enters into the inlet 144A of the fragrant material receiving cassette 141 from the air distribution port 139A, however, most of the air passes through the fragrant smell outlet 139B and a front surface of the outlet 144B of the fragrant material receiving cassette 141 so as to take into the fragrant smell within the cassette 141 from the outlet 144B and the fragrant smell outlet 139B, and becomes an air fragrance generated by mixing with the fragrant smell so as to be blown out from the fragrant smell blowing port 148.

In accordance with the present embodiment, the following effects can be obtained.

(1) The outlet 144B of the fragrant material receiving cassette 141 is arranged in the immediately upstream side of the fragrant smell blowing port 148 in the blowing passage 147. Accordingly, the fragrant smell is discharged to the external without being in contact with most of the blowing chamber 135 provided with the fan 126 and the blowing passage 147, and is not adhered to the blowing chamber 135, the blowing passage 147 and the like. Accordingly, when replacing the fragrant material receiving cassette 141 by a different fragrant material receiving cassette, it is possible to interest a pure fragrant smell of a new fragrant material 1 immediately after the replacement.

(2) Since the outlet 144B of the fragrant material receiving cassette 141 is provided in the upper portion of the cassette 141, the fragrant smell does not leak to the side of the blowing passage 147 and the blowing chamber 135 from the cassette 141 due to the gravity, and is not adhered to the blowing passage 147, the blowing chamber 135 and the like.

Industrial Applicability

As mentioned above, in accordance with the present invention, in the air fragrance device, it is possible to blow out the fragrant smell immediately after driving the fan by the motor.

What is claimed is:

1. An air fragrance device comprising:
   a fan driven by a motor and provided in a blowing chamber;
   an air fragrance tank having a fragrant agent therein and communicated with the blowing chamber; and
   a fragrant smell intake opening,
   wherein the blowing chamber is arranged below the air fragrance tank, and
   wherein the fragrant smell intake opening is located inside the outer periphery of the fan and is configured to transmit a fragrant smell generated by the fragrant agent from the air fragrance tank to the blowing chamber.

2. An air fragrance device as claimed in claim 1, wherein a chamber in which said motor is arranged is shielded with respect to the blowing path.

3. An air fragrance device as claimed in claim 1, wherein an air intake passage and a fragrant smell intake passage with respect to the suction port of said fan are separately formed, and an air and a fragrant smell supplied from both the intake passages are mixed so as to be blown out from the blowing port of the fan.

4. An air fragrance device as claimed in claim 3, wherein a valve for adjusting a fragrant smell flow amount is provided in said fragrant smell intake passage.

5. An air fragrance device as claimed in claim 1, wherein an air storage portion is provided in an immediately upstream side of the suction port of the blowing chamber in which said fan is provided, and a narrow air intake passage provided around the fragrant material receiving portion is communicated with said air storage portion.

6. An air fragrance device as claimed in claim 1, wherein an outlet of the receiving portion for said fragrant agent is arranged in an immediately upstream side of the fragrant smell blowing port to an exterior of the air fragrance device in the blowing passage of the fan.

7. An air fragrance device as claimed in claim 1, wherein an outlet of the receiving portion for said fragrant agent is provided above said receiving portion.

8. An air fragrance device comprising:
   a fan driven by a motor and provided in a blowing chamber; and
   an air fragrance tank having a fragrant agent therein and communicated with the blowing chamber,
   wherein the blowing chamber is arranged below the air fragrance tank,
   wherein an air intake passage and a fragrant smell intake passage with respect to the suction port of said fan are separately formed, and an air and a fragrant smell supplied from both the intake passages are mixed so as to be blown out from the blowing port of the fan, and
   wherein a valve for adjusting a fragrant smell flow amount is provided in said fragrant smell intake passage.

9. An air fragrance device comprising:
   a fan driven by a motor and provided in a blowing chamber; and
   an air fragrance tank having a fragrant agent therein and communicated with the blowing chamber,
   wherein the blowing chamber is arranged below the air fragrance tank, and
   wherein an air storage portion is provided in an immediately upstream side of the suction port of the blowing chamber in which said fan is provided, and a narrow air intake passage provided around the fragrant material receiving portion is communicated with said air storage portion.

10. An air fragrance device comprising:
    a fan driven by a motor and provided in a blowing chamber; and
    an air fragrance tank having a fragrant agent therein and communicated with the blowing chamber,
    wherein the blowing chamber is arranged below the air fragrance tank,
    wherein an outlet of the receiving portion for said fragrant agent is arranged in an immediately upstream side of the fragrant smell blowing port to an exterior of the air fragrance device in the blowing passage of the fan, and
    wherein an outlet of the receiving portion for said fragrant agent is provided above said receiving portion.

* * * * *